United States Patent
Fu et al.

(10) Patent No.: US 10,675,317 B2
(45) Date of Patent: Jun. 9, 2020

(54) USE OF GINSENG EXTRACT, GINSENOSIDE AND GINSENOSIDE DERIVATIVE IN THE PREPARATION OF MEDICINE OR HEALTH CARE PRODUCT FOR TREATING CYTOMEGALOVIRUS INFECTION DISORDERS

(71) Applicant: Li Fu, Liaoning (CN)

(72) Inventors: Li Fu, Liaoning (CN); Kaiqian Wang, Liaoning (CN); Min Hui, Liaoning (CN); Fan Li, Liaoning (CN); Hongyu Fan, Liaoning (CN); Shuo Wang, Liaoning (CN)

(73) Assignee: Li Fu, Liaoning (CN)

( * ) Notice: Subject to any disclaimer, the term of this patent is extended or adjusted under 35 U.S.C. 154(b) by 11 days.

(21) Appl. No.: 15/574,238

(22) PCT Filed: Apr. 21, 2016

(86) PCT No.: PCT/CN2016/079844
§ 371 (c)(1),
(2) Date: Nov. 15, 2017

(87) PCT Pub. No.: WO2016/184290
PCT Pub. Date: Nov. 24, 2016

(65) Prior Publication Data
US 2018/0133273 A1    May 17, 2018

(30) Foreign Application Priority Data

May 15, 2015    (CN) .................. 2015 1 02504445

(51) Int. Cl.
*A61K 36/258* (2006.01)
*A61K 36/00* (2006.01)
*A61K 36/9068* (2006.01)
*A61P 31/20* (2006.01)
*A61K 31/704* (2006.01)
*A61K 45/06* (2006.01)

(52) U.S. Cl.
CPC .......... *A61K 36/258* (2013.01); *A61K 31/704* (2013.01); *A61K 36/9068* (2013.01); *A61K 45/06* (2013.01); *A61P 31/20* (2018.01)

(58) Field of Classification Search
None
See application file for complete search history.

(56) References Cited

FOREIGN PATENT DOCUMENTS

| CN | 102166238 A | * | 8/2011 |
|---|---|---|---|
| CN | 103536884 | | 1/2014 |
| CN | 104523790 A | * | 4/2015 |
| WO | 00/50054 | | 8/2000 |

OTHER PUBLICATIONS

An, Ning et al. "Effect of Ginsenoside Rg3 on Protein Expression of Lung Cancer Cell Line", Chinese Journal of Lung Cancer, vol. 11, No. 3, Jun. 30, 2008 (Jun. 30, 2008), ISSN: 1009-3419, article abstract, page 312, left column, paragraph 1.

* cited by examiner

*Primary Examiner* — Michael Barker
*Assistant Examiner* — Randall Winston
(74) *Attorney, Agent, or Firm* — Boyle Fredrickson S.C.

(57) ABSTRACT

The invention discloses new application of a ginseng extract, ginsenoside and a ginsenoside derivative in the preparation of a medicine for treating HCMV infection related diseases. The related diseases comprise HCMV infection caused in the process of treating cardiovascular and cerebrovascular diseases, organ transplantation, perinatal periods, tumors, burn, AIDS and other diseases of patients. Tests prove that the ginseng extract, the ginsenoside and the ginsenoside derivative have a remarkable curative effect, quick response and a small toxic or side effect during treatment of HCMV infected diseases, are a medicine or a health product for treating the HCMV infection, which is safe, efficient and stable and has a simple preparation process, and are suitable for industrial production and easy to popularize. In the invention, a new medicine source is provided for the treatment of the HCMV infection.

4 Claims, No Drawings

USE OF GINSENG EXTRACT, GINSENOSIDE AND GINSENOSIDE DERIVATIVE IN THE PREPARATION OF MEDICINE OR HEALTH CARE PRODUCT FOR TREATING CYTOMEGALOVIRUS INFECTION DISORDERS

TECHNICAL FIELD

The invention belongs to the field of medicines, and relates to a medicine or health food for treating human cytomegalovirus infection, particularly to application of ginseng (a traditional Chinese medicine) extracts and derivatives thereof in medicines or health foods for treating cytomegalovirus infection.

BACKGROUND ART

Human Cytomegalovirus (HCMV) also known as cellular inclusion body virus is named for the swelling of infected cells and the possession of huge intranuclear inclusions. The HCMV belongs to β herpes virus subfamilies, with the diameter of about 200 nm, is one of the largest animal viruses, and has a 64 nm inner core containing virus DNA, with a 110 nm icosahedrons coated outside. An integrated particle is wrapped by an envelope in which BJ consists of protein or glycoprotein encoded by 25-30 virus particles at least. The HCMV has the genome length of 235-240 kb and the molecular weight of $150-160*10^3$ kDa as well as linear double-stranded DNA, and belongs to DNA viruses. HCMV consists of long (L) and short (S) compositions or segments. Due to different directions or inversion at the mutual junction of the two compositions, the structures of DNA molecules have 4 homogenous isomers. Because of its wide distribution, other animals can be infected to cause various kinds of system infection from slight asymptomatic infection to serious defects or death mainly based on a genitourinary system, a central nervous system and liver diseases.

An HCMV gene structurally contains polypeptide segments encoding 3 infection cell specificities, namely an immediate early protein region, an early protein region and a later protein region, with 3 kinds of protein having immunogenicity and time phases. HCMV transcription-translation is regulated and controlled by HCMV and host cells. The expression of immediate early genes and early genes is regulated and controlled by promoters, which are commonly detected as acute infection. The transcription and translation of later genes are regulated and controlled by IE and E genes and protein, which marks the incubation period of viruses after detection. The maturity of virus assemblies is an anaphase result of HCMV infection. An HCMV genome has 3 morphological transforming regions inducing cell transformation, namely mtr I, mtr II and mtr III. The mtr I is positioned on the E fragment of Hind III at the tail end of the left side of an ADI69 strain genome U, has the length of 588 bp and can be used for transforming NIH3T3 and primary rat embryo cells. The mtr II is positioned on the Xbal/Bam HI EM fragment of DNA from an HCMV Towne strain, has the length of 980 bp and can transform NIH3T3 and rat-2 cells; ADI69 and TdCMv Tanaka strains of the HCMV have areas corresponding to the strains which contain 2 separated promoters, P1 and P2; and all the transformed cells and tumor cells formed therefrom exist in the mtr II. The mtr III is positioned on an Xbal/BamHI segment, and can be used for encoding main immediate early protein with the molecular weight of 72 kD; the protein is related to trans-activation and auto-regulation of viruses; and the mtr III does not exist in transformed cells.

From the view of cellular levels, infection is divided into three kinds: a. toxigenic infection; b. latent infection; and c. cell transformation or latent carcinogenic infection. The HCMV from an in-vitro test can form a cell strain with virus antigens after being inoculated to a human fibroblast, and has the characteristics of transformed cells. Transfection cells can be extracted from a specific fragment of HCMV-DNA; and partial cells can be integrated to cell chromosome DNA through DNA to transform and are inoculated to an athymic naked mouse to generate tumors. An HPV immortalized human cervical epithelial cell line established by applying HCMV IE transfection through Chaoqi Liu and the like gets the result that the HCMV can promote malignant transformation of cervical epithelial cells in cooperation with HPV16 and form the tumors in the naked mouse after being integrated into a cell chromosome, which explains the close relationship between the HCMV and cervical cancers. The HCMV inactivated by using ultraviolet rays through Deyin Lu and the like is inoculated to the cervical part of the mouse for 3 times per week, totally 8 weeks. Results show that an HCMV group has the cervical precancerous lesion rate of 27.8% (23/83) and the cancer incidence rate of 20.5% (17/83).

Cytomegalovirus (CMV) has a typical herpes virus morphology, with a DNA structure being similar with that of HSV but 5% larger than that of the HSV. The virus has high species specificity from hosts or culture cells. The HCMV can only infect humans and proliferate in human fibroblasts. Viruses proliferate slowly in cell culture, have a long replicative cycle, and can generate cytopathic effects after 30-40 days during primary segregation. The CMV is characterized by cell swelling and rounding, nucleus enlarging and a large acidophilic inclusion body rounded by a "Halo" in a nucleus. The cellular immune function of an organism plays an important role in the generation and development of CMV infection. People with cellular immunity deficiencies can be subjected to serious CMV infection for a long term, as well as further inhibition on the cellular immunity of the organism, such as activity decrease of cytotoxic T cells, functional reduction of NK cells and the like. The organism can generate specific antibodies and cytotoxic T lymphocytes after primary infection from the CMV to activate NM cells. The antibodies have the capacity of limiting CMV replication as well as a certain resistance to reinfection from the same strain but cannot resist to the excitation of endogenous latent viruses and exogenous infection from other different strains of the CMV. However, the cells can give play to the maximum antiviral effect through the toxicity of specificity cytotoxic T lymphocytes and antibody-dependent cells.

The HCMV infection is very common in a crowd, and can cause various diseases. Adult infection is caused frequently in the states of immune deficiencies or immune inhibition. Particularly, the HCMV infection is very easily caused frequently after immunosuppressive agent treatment is received during organ transplantation and bone marrow transplantation as well as malignant tumor patients receive radiotherapy and chemotherapy. AIDS patients are extremely high in the morbidity of the HCMV infection. The HCMV infection is highly valued worldwide due to universality and possible serious consequences, which has a very important significance for the fundamental research of epidemiology, diagnostic techniques, treatment and prevention as well as related virology about the HCMV infection. The immunologic function of tumor patients is greatly lower than that of normal persons after the receiving of the chemotherapy or the radiotherapy. Latent HCMV is easy to reactivate to cause serious infection, which is an important infection factor of influencing the survival rate and the living quality of the tumor patients.

CMV infection disease is congenital or acquired infection caused by the CMV. In the congenital or acquired infection caused by the CMV, the CMV is a double-stranded DNA virus which belongs to a herpes virus group and has a form similar to that of other herpes viruses as well as obvious species specificity from the hosts or tissue culture cells. The HCMV can only be separated and cultured in human embryo fibroblasts.

The HCMV infection is very wide in the crowd. The infection rate of adults in China reaches over 95%. The adult infection is caused frequently in the states of the immune deficiencies or the immune inhibition. Particularly, the HCMV infection is very easily caused frequently after the immunosuppressive agent treatment is received during organ transplantation and bone marrow transplantation as well as the malignant tumor patients receiving the radiotherapy and the chemotherapy. Most of infected persons do not have clinical symptoms, but serious diseases can be generated by affecting multiple organs and systems under a certain condition. The viruses can invade lungs, livers, kidneys, salivary glands, mammary glands and other glands as well as multinuclear leukocytes and lymphocytes, can be excreted from saliva, human milk, sweat, blood, urine, sperm, uterine secretion and other parts for a long term or at intervals, and are usually spread by oral cavities, genital tracts, placentas, blood transfusion or the organ transplantation and other ways.

(I) Congenital infection: the HCMV infection of pregnant maternal bodies can invade fetuses through placentas to cause the congenital infection and a small amount of premature birth, abortion, stillbirth or postnatal death. Child patients can suffer from jaundice, hepatosplenomegaly, thrombocytopenic purpura and hemolytic anemia. Survived children usually leave over permanent mental retardation, neuromuscular dyskinesia, deafness, chorioretinitis and the like.

(II) Perinatal infection: the HCMV is excreted by urinary tracts and cervices of parturients, then infants can be infected through birth canals during childbirth, most of which has slight symptoms or subclinical infection without clinical symptoms and some of which has slight respiratory tract obstacles or liver function impairments.

(III) Children and adult infection: a subclinical type is usually caused by the infection of milk absorbing, kisses, sexual contact, blood transfusion and the like, which may also cause negative mononucleosis of heterophil antibodies sometimes. The viruses hidden in monocytes and the lymphocytes can be activated by receiving immunosuppressive therapy, the organ transplantation, tumors and other factors during pregnancy, which can cause mononucleosis, hepatitis, interstitial pneumonia, retinitis, encephalitis and the like.

(IV) Cell transformation and possible carcinogeneses: fibroblasts of rodent embryos can be transformed by the HCMV inactivated by the ultraviolet rays. The HCMV in certain tumors such as cervical cancer, colon cancer, prostate cancer and kaposis sarcoma is high in the detection rate of DNA and has the antibody titer higher than that of normal persons. Virus particles are also discovered in cell strains established by the tumors, to prompt that the HCMV has potential carcinogenic possibilities the same as herpes viruses of the HCMV. The immunologic function of the tumor patients is greatly lower than that of the normal persons after the receiving of the chemotherapy or the radiotherapy. The latent HCMV is easy to reactivate to cause the serious infection, which is the important infection factor of influencing the survival rate and the living quality of the tumor patients.

Most of HCMV infected patients are in a state of latent infection, so that asymptomatic infection can be avoided frequently even if the HCMV has duplicate activities in vivo. At present, effective and safe anti-HCMV medicines are not available, so the treatment of the HCMV infection is still limited to expectant treatment during symptomatic infection; ganciclovir can only be cautiously used for symptomatic infection because of myelosuppression and other toxic or side effects. Ganciclovir DHPG has an effect of preventing the HCMV from diffusing, and can reduce the death rate of HCMV pneumonia complications of the bone marrow transplantation if being used together with high-titer anti-HCMV immune globulin. Foscarnet sodium can be selected for the HCMV infection resisting to the Ganciclovir DHPG, and has an effect lower than that of the Ganciclovir DHPG although the diffusion of the HCMV can be reduced permanently. HCMV live viral vaccines developed abroad can induce antibody production, but the problem of excluding the oncogenic potential of the vaccines needs to be solved.

Panax ginseng C. A. Mey. (i.e. Ginseng), a traditional Chinese medicine, is a precious medicinal material. Ginsenoside, as a main active ingredient of the ginseng, is widely researched and used. In the ginsenoside, ginseng extracts and derivatives thereof are the most impressive. As the main active ingredient of the ginseng, the ginsenoside with good safety has been prepared into anti-tumor oral preparations applied clinically, and been researched deeply as an injection.

Due to the adoption of an advanced separation and purification technology, the inventor extracts the ginseng extracts and the derivatives thereof serving as active ingredients for treating the HCMV infection, from a ginseng medicinal material, by a large quantity of modern scientific researches, and carries out pharmacodynamical and pharmacological research for treating the HCMV infection on the ginseng extracts and the derivatives and corresponding medicinal preparations thereof. Results prove that the ginseng extracts and derivative monomers thereof have clear pharmacological effects, a strong effect of treating the HCMV infection, low toxic or side effects and high safety, and can provide an efficient low-toxicity medicine for treating the HCMV infection.

SUMMARY OF THE INVENTION

To solve the above technical problems in treatment of the HCMV infection disease, an object of the present invention is to provide a novel use of ginseng extracts, ginsenoside or ginsenoside derivatives in preparation of drugs or health products for treating human cytomegalovirus (HCMV) infection disease. The ginseng extracts, the ginsenoside and the ginsenoside derivatives have the performance and effect of treating HCMV infection.

To achieve the above object, the invention, in one aspect, provides a use of a ginseng extract, ginsenoside or a ginsenoside derivative in the preparation of a drug or a health product for treating the HCMV infection disease.

Wherein related diseases caused by the HCMV infection comprise the diseases caused by the HCMV infection in the process of treating cardiovascular and cerebrovascular diseases, tumors, burn, AIDS, organ transplantation or perinatal periods and the like.

In the process of screening natural active components that are effective in treating the HCMV infection, the inventor found that the chemical ingredients of ginseng which are the ginseng extracts, the ginsenoside and the ginsenoside derivatives have a strong effect of treating the HCMV infection.

Wherein the medicine consists of the ginseng extract, ginsenoside or ginsenoside derivative and a pharmaceutically acceptable carrier.

Particularly, the ginseng extract is selected from a ginseng alcohol extract and a ginseng water extract; the ginsenoside is total ginsenoside ginseng root, panaxdiol type ginsenoside and 20(R)-ginsenoside rg3; and the ginsenoside derivative is a 20(R)-ginsenoside rg3 derivative.

Especially, the ginsenoside rg3 derivative is 20(R)-ginsenoside Rg3 8-N-butyrate, with the molecular formula of $C_{86}H_{144}O_{21}$ and the structural formula shown in formula (I):

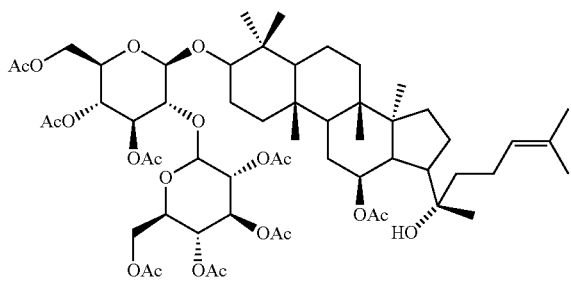

(I)

Wherein the ginseng alcohol extract is prepared according to the following steps:

1) Mixing the herb of Panax ginseng C. A. Mey. with an extraction solvent uniformly, and carrying out soaking treatment;

2) Heating extraction on the soaked mixture of the ginseng and the extraction solvent, and filtering and collecting extraction liquid;

3) Concentrating the collected extraction liquid into extractum, and then drying the extractum to obtain the ginseng alcohol extract.

Particularly, the soaking treatment time in the step 1) is 30-60 min, preferably 30 min.

Especially, the weigh rate of the ginseng medicinal material to the extraction solvent is 1:8-12, preferably 1:10.

The ginseng medicinal material in the invention is also called the herb of Panax ginseng C. A. Mey.

Particularly, the extraction solvent is an ethanol solution with the volume percentage concentration of ≥50%, preferably a 50-75% ethanol solution.

Wherein the heating extraction times in the step 2) is 2-3 times, preferably 3 times.

Particularly, in each heating extraction process, the weight ratio of the ginseng medicinal material and the extracting solvent is 1:8-12, preferably 1:8; the temperature for each heating and extracting is 60-80° C., preferably 70° C.; and the heating extraction time is 0.5-2 h, preferably 1 h.

Wherein in the step 3), the concentration temperature of the concentration process is 65-85° C., preferably 80° C.; the relative density of the concentrated extractum is 1.05-1.15, preferably 1.1; and the drying temperature is 70-90° C., preferably 85° C.

Particularly, the content of the total ginsenoside in the ginseng alcohol extract is 2-5% (detection method according to the national standard: GB/T19506-2009 Appendix B).

Wherein the ginseng water extract is prepared according to the following steps of:

1) soaking the Panax ginseng C. A. Mey. in water;

2) Carrying out decoction extraction on the soaked mixture of the Panax ginseng C. A. Mey. and the water, and filtering and collecting extraction liquid;

3) Concentrating the extraction liquid into extractum, and then drying the extractum to obtain the ginseng water extract.

Particularly, in the step 1), the soaking treatment time is 30-60 min, preferably 30 min.

Especially, the weight ratio of the Panax ginseng C. A. Mey. to the water is 1:8-12, preferably 1:10.

Wherein the decoction extraction times in the step 2) is 2-3 times, preferably 3 times.

Particularly, in each decoction extraction process, the weight ratio of the ginseng medicinal material to the water is 1:8-12, preferably 1:8; the decoction extraction temperature is 90-100° C., preferably 90-95° C.; and the decoction extraction time is 0.5-2 h, preferably 1 h.

Wherein the concentration temperature in the step 3) is 70-95° C., preferably 80° C.; the relative density of the extractum is 1.05-1.15, preferably 1.1; and the drying temperature is 70-95° C., preferably 85° C.

Particularly, the content of the total ginsenoside in the ginseng water extract is 2-5% (detection method according to the national standard: GB/T19506-2009 Appendix B).

Wherein the total ginsenoside ginseng root is prepared according to the following steps of:

1) Mixing the ginseng medicinal material with the extraction solvent uniformly, and carrying out soaking treatment;

2) Heating extraction on the soaked mixture of the ginseng and the extraction solvent, and filtering and collecting extraction liquid;

3) Carrying out macroporous resin separation to the ginseng extraction liquid, and collecting and combining eluent to obtain ginseng-resin column eluent;

4) Concentrating and drying the ginseng-resin column eluent to obtain the total ginsenosideginseng root.

Particularly, the soaking time in the step 1) is 30-60 min, preferably 30 min.

Especially, the weight ratio of the ginseng medicinal material to the extraction solvent is 1:8-12, preferably 1:10.

Particularly, the extraction solvent is the ethanol solution with the volume percentage concentration of preferably the 50-75% ethanol solution.

Wherein the times of heating extraction in the step 2) is 2-3 times, preferably 3 times.

Particularly, in each heating extraction process, the weight ratio of the ginseng medicinal material to the extraction solvent is 1:8-12, preferably 1:8; the heating extraction temperature each time is 60-80° C., preferably 70° C.; and the heating extraction time is 0.5-2 h, preferably 1 h.

Particularly, the method further comprises concentrating the ginseng extract collected in step 2) to obtain a ginseng concentrate, and then carrying out the macroporous resin column separation.

Especially, the ginseng concentrate contains, per milliliter, 1-3.5 g of ginseng crude medicinal material, which is equivalent to 1-3.5 g ginseng crude medicinal material/ml ginseng concentrate, preferably 2.5 g ginseng crude medicinal material/ml ginseng concentrate.

Wherein the macroporous resin column chromatography in the step 3) comprises the following sequential steps: 3A)

adding the ginseng extraction liquid in the macroporous resin column, and then eluting the macroporous resin column with water as eluent; and 3B) eluting the macroporous resin column with ethanol solution which the volume percentage of the ethanol solution is 30% -50% (v/v) as eluent, collecting fluid from the macroporous resin column after eluting, to obtain ginseng resin eluent.

Particularly, during the macroporous resin column chromatography, the ratio of ginseng weight in ginseng extract to macroporous resin volume was 1:0.8-2.5, preferably 1:1.

Especially, during the macroporous resin separation, the ratio of the column diameter of the macroporous resin column to the column height of the resin is 1:5-10, preferably 1:5-7, further preferably 1:5.5-5.9.

Wherein the macroporous adsorption resin in the step 3) is selected from one of X-5, AB-8, NK-2, NKA-2, NK-9, D3520, D101 and WLD, preferably D101.

Particularly, the ratio of the weight of water used in step 3A) to the column volume of the macroporous resin column is 2-4:1, preferably 4:1; in step 3B), the ratio of the weight of the ethanol solution (30%-50%, v/v) to the volume of the macroporous resin is 2-8:1, preferably 4-8:1, further preferably 8:1, Especially, in the step 3B), the volume percentage concentration of the ethanol solution serving as the eluent is 50%.

Wherein the concentration temperature in the step 4) is 65-90° C., preferably 80° C.; and the drying temperature is 75-95° C., preferably 85° C.

Particularly, the content of the total ginsenoside in the total ginsenoside ginseng Root is 20-50% (detection method according to national standard: GB/T19506-2009 Appendix B).

Wherein the Panaxadiol type ginsenoside is prepared according to the following steps:

1) Mixing the ginseng medicinal material with the extraction solvent uniformly, and carrying out soaking treatment to obtain soaked mixture;

2) Heating extraction on the soaked mixture, and filtering and collecting extraction liquid;

3) Carrying out the first macroporous resin chromatography separation to the ginseng extraction liquid, and collecting and combining the eluent to obtain the first ginseng-resin column eluent;

4) Carrying out the second macroporous resin chromatography separation to the first ginseng-resin column eluent, and collecting and combining the eluent to obtain the second ginseng-resin column eluent;

5) Concentrating and drying the second ginseng-resin column eluent to obtain the Panaxadiol type ginsenoside.

Particularly, the soaking time in the step 1) is 30-60 min, preferably 30 min.

Especially, the weight ratio of the ginseng medicinal material to the extraction solvent is 1:8-12, preferably 1:10.

Particularly, the extraction solvent is the ethanol solution with the volume percentage concentration of ≥50%, preferably the 50-75% ethanol solution.

Wherein the heating extraction times in the step 2) is 2-3 times, preferably 3 times.

Particularly, in each heating extraction process, the weight ratio of the ginseng medicinal material to the extraction solvent is 1:8-12, preferably 1:8; the heating extraction temperature each time is 60-80° C., preferably 70° C.; and the heating extraction time is 0.5-2 h, preferably 1 h.

Particularly, the method further comprises a step 2A): concentrating the ginseng extraction liquid collected in step 2) to obtain a ginseng concentrated liquid, and then carrying out the macroporous resin column separation.

Especially, the ginseng concentrated liquid contains, per milliliter, 1-3.5 g of ginseng crude medicinal material, which is equivalent to 1-3.5 g ginseng crude medicinal material/ml ginseng concentrated liquid, preferably 2.5 g ginseng crude medicinal material/ml ginseng concentrated liquid.

Wherein the first macroporous resin column chromatography in the step 3) comprises the following sequential steps: 3A) adding the ginseng extraction liquid in the macroporous resin column, and then eluting with water as an eluant; and 3B) eluting the macroporous resin column with ethanol solution which the volum percentage of the ethanol solution is 30% -50% (v/v) as eluent, collecting fluid from the macroporous resin column after eluting, to obtain the first ginseng-resin column eluent.

Particularly, during macroporous resin column chromatography, the ratio of the weight of the ginseng in the ginseng extraction liquid to the volume of macroporous resin is 1:0.8-2.5, preferably 1:1.

Especially, during macroporous resin separation, the ratio of the column diameter of the macroporous resin column to the column height of the resin is 1:5-10, preferably 1:5-7, further preferably 1:5.5-5.9.

Wherein the macroporous adsorption resin in the step 3) is selected from one of X-5, AB-8, NK-2, NKA-2, NK-9, D3520, D101 and WLD, preferably D101.

Particularly, the ratio of the amount of water used in step 3A) to the column volume of the macroporous resin column is 2-4:1, preferably 4:1; in step 3B), the ratio of the ethanol solution (30%-50%, v/v) to the column volume of the macroporous resin column is 2-8:1, preferably 4-8:1, further preferably 8:1.

Especially, in the step 3B), the volume percentage concentration of the ethanol solution serving as the eluant is 50%.

Particularly, the method further comprises concentrating the first ginseng-resin column eluent collected in the step 3) to obtain the first ginseng-resin concentrated liquid, and then carrying out the second macroporous resin chromatography separation.

Especially, the first ginseng-resin concentrated liquid contains, per milliliter, 3.5-6 g of ginseng crude medicinal material, which is equivalent to 3.5-6 g ginseng crude medicinal material/ml ginseng concentrated liquid, preferably 5.0 g ginseng crude medicinal material/ml ginseng concentrated liquid.

Particularly, the second macroporous resin column chromatography in the step 4) comprises the following steps in sequence: 4A) adding the first ginseng-resin column eluent into the macroporous resin column, and then eluting with ethanol solution (50-60%, v/v) as an eluant; and 4B) eluting with ethanol solution (70-80%, v/v) as the eluant, and collecting fluid from the macroporous resin column after eluting, to obtain the second ginseng-resin column eluent.

Particularly, during the second macroporous resin column chromatography in the step 4), the ratio of the weight of the ginseng in the first ginseng-resins column eluent to the volume of the macroporous resin is 1:0.8-2.5, preferably 1:1.

Especially, during macroporous resin separation, the ratio of the column diameter of the macroporous resin column to the column height of the resin is 1:5-10, preferably 1:5-7, further preferably 1:5.5-5.9.

Wherein the macroporous adsorption resin in the step 4) is selected from one of HPD-200, D203, XAD-4 and HPD-100, preferably HPD-100.

Particularly, the ratio of the weight of the ethanol solution (50-60%, v/v) in the step 4A) to the column volume of the macroporous resin column is 2-4:1, preferably 4:1; and in the step 4B), the ratio of the weight of the ethanol solution (70-80%, v/v) to the column volume of the macroporous resin column is 2-8:1, preferably 4-8:1, further preferably 8:1.

Wherein the concentration temperature in the step 5) is 65-95° C., preferably 80° C.; and the temperature in the drying process is 70-95° C., preferably 85° C.

Particularly, the content of the total Panaxadiol Saponin (PDS) in the Panaxadiol type ginsenoside is 30-70% (detection method: detection according to methods in Appendix B of national standard GB/T19506-2009).

Wherein the content of the 20(R)-ginsenoside Rg3 is 1%-98%, preferably 30-80%, further preferably 60%.

Particularly, the content of the 20(R)-ginsenoside Rg3 is ≥1%, preferably ≥30%, further preferably ≥60%, more further preferably ≥80%, much more further preferably ≥98%.

Wherein the content of the 20(R)-ginsenoside Rg3 derivative is 1%-98%, preferably 30-80%, further preferably 60%.

Particularly, the content of the 20(R)-ginsenoside Rg3 derivative is ≥1%, preferably ≥30%, further preferably ≥60%, more further preferably ≥80%, much more further preferably ≥98%.

Wherein the content of the total ginsenoside in the ginseng alcohol extract is 2-5%; the content of the total ginsenoside in the ginseng water extract is 2-5%; the content of the total ginsenoside in the total ginsenoside ginseng root is 20-50%; and the content of panaxadiol saponin in the panaxdiol type ginsenoside is 30-70%.

Particularly, pharmaceutically acceptable carrier is generally considered by healthcare professionals to be able to achieve this purpose and serve as a non-active component of drugs. The corpus of the pharmaceutically acceptable carriers can be found in reference books, such as, *Handbook of Pharmaceutical excipients,* 2nd Edition, edited by A. Wade and P. J. Weller, published by American Pharmaceutical Association, Washington and the Pharmaceutical Press, London, 1994.

Particularly, the carriers comprise excipients such as starch, water and the like; lubricants such as magnesium stearate and the like; disintegrants such as microcrystalline cellulose and the like; fillers such as lactose and the like; binders such as pregelatinized starch, dextrin and the like; sweetening agents; antioxidants; and preservatives, flavoring agents, flavors and the like;

Wherein the medicine exists in the forms of tablets, capsules, pills, powder, granules, syrups, solutions, emulsions, injections, sprays, aerosols, gels, creams, tinctures, cataplasm, rubber emplastrum or emplastrum.

The invention, on the other hand, provides a medicament or a health product for treating the HCMV infection disease, which contains the ginseng extract, the ginsenoside or the ginsenoside derivative.

Wherein the ginseng extract is selected from the ginseng alcohol extract and the ginseng water extract; the ginsenoside is the total ginsenoside ginseng root, the panaxdiol type ginsenoside and the 20(R)-ginsenoside rg3; and the ginsenoside derivative is the 20(R)-ginsenoside rg3 derivative.

Particularly, the ginsenoside rg3 derivative is the 20(R)-ginsenoside Rg3 8-N-butyrate.

Wherein the content of the 20(R)-ginsenoside Rg3 is 1%-98%, preferably 30-80%, further preferably 60%.

Particularly, the content of the 20(R)-ginsenoside Rg3 is ≥1%, preferably ≥30%, further preferably ≥60%, more further preferably ≥80%, much more further preferably ≥98%.

Wherein the content of the 20(R)-ginsenoside Rg3 derivative is 1%-98%, preferably 30-80%, further preferably 60%.

Particularly, the content of the 20(R)-ginsenoside Rg3 derivative is ≥1%, preferably ≥30%, further preferably ≥60%, more further preferably ≥80%, much more further preferably ≥98%.

Wherein the content of the total ginsenoside in the ginseng alcohol extract is 2-5%; the content of the total ginsenoside in the ginseng water extract is 2-5%; the content of the total ginsenoside in the total ginsenoside ginseng root is 20-50%; and the content of the panaxadiol saponin in the panxdiol type ginsenoside is 30-70%.

Particularly, the ratio of the weight of the ginseng extract, the ginsenoside or the ginsenoside derivative to the total weight of the medicine or the health product is 0.01-10:100, preferably 0.1-10:100, further preferably 1-10:100.

Particularly, the medicine or the health product also comprises one or more of a Radix Sophorae Tonkinensis extract, Fructus Xanthii extract, Herba Scutellariae barbatae extract, Radix Sophorae flavescentis extract, Herba Taraxaci extract, Flos Lonicerae extract, *Zingiber officinale* Rosc. Extract, a grape seed extract, a pomegranate seed extract, vitamin C and its derivatives thereof or vitamin E and its derivatives thereof.

The drug can be prepared into different pharmaceutical preparations, such as tablets, capsules, pills, powders, granules, syrups, solutions, emulsions, injections, sprays, aerosols, gels, creams, cataplasms, rubber plasters or patches, by using a commonly known method in the art.

The drug can be prepared into different pharmaceutical preparations, such as tablets, capsules, pills, powders, granules, syrups, solutions, emulsions, injections, sprays, aerosols, gels, creams, tinctures, cataplasm, rubber emplastrum or emplastrum, by using a commonly known method in the art.

The invention also provides a method for treating the HCMV infection disease, including administering a therapeutically effective amount of a pharmaceutical medicine of ginseng extract, the ginsenoside or the ginsenoside derivative to a patient, the therapeutically effective dosage is 0.6-12 mg/kg·d, preferably 1-6 mg/kg·d, further preferably 1.5-3 mg/kg·d.

Unless otherwise indicated, the term "therapeutically effective dosage" used herein is the dosage of the drug desired for producing the efficacy; the "therapeutically effective dosage" may be adjusted and varied, finally determined by the medical staff, depending on the factors considered, including the route of administration, the property of preparation, recipient's weight, age and other general conditions, and the nature and severity of diseases to be treated.

Compared with the prior art, the invention has the following obvious advantages:

1. The invention has developed new medicinal value of the ginseng extracts, the ginsenoside or the ginsenoside derivatives which are used for treating related diseases of the HCMV infection. The related diseases comprise the HCMV infection of patients in the process of treating cardiovascular and cerebrovascular diseases, organ transplantation, perinatal periods, tumors, burn, AIDS and other diseases, particularly the HCMV infection in the states of the immune deficiencies or the immune inhibition after immunosuppressive agent treatment is received during organ transplantation and bone marrow transplantation as well as the malignant tumor patients receive the radiotherapy and the chemotherapy. In addition, the ginseng extracts, the ginsenoside or the ginsenoside derivatives can be used for preparing the medicines or the health foods for treating the HCMV infection, thus developing a new field for the application of ginseng medicinal materials.

2. A series of experimental researches of the invention prove that the ginseng extracts, the ginsenoside or the ginsenoside derivatives have a remarkable effect of preventing and treating the HCMV infection.

3. The ginseng extracts, the ginsenoside or the ginsenoside derivatives of the invention have strong pharmacological effects, a remarkable effect of treating the HCMV infection, quick response, small toxic or side effects, high safety as well as a good medicinal prospect, and can be used for a long term.

4. The products of the invention have abundant and cheap resources, safe clinical use, simple preparation process and small dosing amount, can be prepared into various formulations, and are convenient to use, thus achieving easy popularization.

5. In the invention, the ginseng extracts, the ginsenoside or the ginsenoside derivatives can be used for preparing the medicines for treating the HCMV infection, and the ginseng extracts, the ginsenoside or the ginsenoside derivatives can be combined with other active ingredients (such as one or more of the tonkin Radix Sophorae flavescentis extract, the siberian cocklebur fruit extract, the Herba Scutellariae barbatae extract, the Radix Sophorae flavescentis extract, the dandelion extract, the honeysuckle flower extract, the *Zingiber officinale* Rosc. extract, the grape seed extract, the pomegranate seed extract, vitamin C and derivatives thereof or vitamin E and derivatives thereof) together, to prepare compound medicines for treating the HCMV infection.

DETAILED DESCRIPTION OF THE INVENTION

The advantages of the present invention are further described below by way of specific embodiments. These examples are merely exemplary and are not intended to limit the scope of the invention. It should be understood by those skilled in the art that modifications or alterations to details and forms of the technical solution of the present invention may be made without departing from the concept and usage scope of the formulations of the present invention; however, all these modifications and alterations fall within the scope of the present invention.

Embodiment 1 Preparing Ginseng Alcohol Extract

1. The First Extraction

The ginseng (300 g) and ethanol solution (3000 g) which the volum percentage of the ethanol solution is 70% (v/v), were added into the multi-functional extraction tank of Chinese traditional medicine. After soaking for 30 min, the multi-functional extraction tank was turned on and heated to carry out the first heating extraction on the ginseng medicinal material. In the first heat extraction process, carrying out constant-temperature extraction at 70° C. for 1 h, and then filtering to obtain the first extraction liquid and the first ginseng residues, wherein the weight ratio of the ginseng to the extraction solvent (the ethanol solution) is 1:10.

In the invention, all the other ratios of 1:8-12 are suitable for the invention besides the weight ratio (1:10) of the ginseng to the extraction solvent; all the other soaking time of ≥30 min are suitable for the invention besides the soaking time of 30 min, preferably 30-60 min; other ethanol solutions with the volume percentage concentration of ≥50% are suitable for the invention besides the ethanol solution (70%, v/v), preferably the ethanol solution with the volume percentage concentration of 50-75% and absolute ethanol; and the extraction temperature of 60-80° C. and the extraction time of 0.5-2 h are suitable for the invention.

2. The Second Extraction

Adding the ethanol solution (70%, v/v) into the first ginseng residues, heating the mixture, carrying out the second heating extraction on the ginseng medicinal material at 70° C. for 1 h, and then filtering to obtain the second extraction liquid and the second ginseng residues, wherein the weight ratio of the ginseng to the extraction solvent is 1:10.

3. The Third Extraction

Adding the ethanol solution (70%, v/v) into the second medicine residues, heating the mixture, carrying out the third heating extraction on the ginseng medicinal material at 70° C. for 1 h, and then filtering to obtain the third extraction liquid, wherein the weight ratio of the ginseng to the extraction solvent is 1:10.

In the embodiment of the invention, all the other ethanol solutions with the volume percentage concentration of ≥50% are suitable for the invention besides the ethanol solution with the volume percentage concentration of 70%, preferably the ethanol solution with the concentration of 50-75% and the absolute ethanol; all the extraction temperatures of 60-80° C. are suitable for the invention; and all the heating extraction time of 0.5-2 h is suitable for the invention.

In the embodiment of the invention, the heating extraction times is 3 in the process of preparing the ginseng alcohol extract, and all the extraction times of 2-3 are suitable for the invention.

4. Condensing and Drying

Combining the first, second and third extraction liquids obtained after filtering, placing the total extraction liquids in a rotary evaporator, and then condensing by evaporation at the temperature of 80° C. to obtained the extractum with the relative density of 1:1, and then drying the extractum to constant weight in an oven at the temperature of 85° C. to obtain the ginseng alcohol extract.

The ginseng alcohol extract is brownish-yellow powder with special smell, soluble in ethanol. The content of the total ginsenoside in the ginseng alcohol extract measured by methods of national standard (ginseng from Jilin Changbai Mountain, a product of geographical indication, which is obtained by methods in Appendix B of GB/T19506-2009) is 3%.

In the condensing process of the ginseng alcohol extract of the present invention, the condensing temperature of 65-85° C. and the relative density of 1.05-1.15 of the concentrated extractum are suitable for the invention; The drying temperature of 70-90° C. is suitable for the invention. The content of the total ginsenoside in the ginseng alcohol extract prepared by the method of the invention is 2-5%.

Embodiment 2 Preparing Ginseng Water Extract

1. Soaking Treatment

Putting the smashed ginseng (300 g), extraction solvent tap water (3,000 g) into the multifunctional traditional Chinese medicine extraction tank, mixing evenly and then soaking; and the weight ratio of the ginseng to the water is 1:10.

During preparation of the ginseng water extract in the invention, all the soaking time of ≥30 min is suitable for the invention, preferably 30-60 min; and all the other weight rate of the ginseng to the water, such as 1:8-12, besides 1:10, are suitable for the invention.

2. The First Extraction

After soaking for 30 min, turning on the power of the multifunctional extraction tank for heating to carry out the first decoction extraction on the ginseng medicinal material, extracting at 95° C. for 1 h, and then filtering to obtain the first extraction liquid and the first ginseng residues;

3. The Second Extraction

Adding the tap water into the first ginseng residues, heating the mixture, carrying out the second decoction extraction at 90° C. for 1 h, and then filtering to obtain the second extraction liquid and the second ginseng residues, wherein the weight proportion of the ginseng to the extraction solvent is 1:10.

4. The Third Extraction

Adding the tap water into the second ginseng residues, heating the mixture, carrying out the third decoction extraction at 90° C. for 1 h, and then filtering to obtain the third extraction liquid, wherein the weight ratio of the ginseng to the extraction solvent is 1:10.

In the embodiment of the invention, all the other weight ratios of the ginseng medicinal material to the extraction solvent water in the first, second and third processes of the ginseng water extract, such as 1:8-12, besides 1:10, are suitable for the invention; all the extraction temperature of 90-100° C. is suitable for the invention, preferably 90-95° C.; and all the heating extraction time of 0.5-2 h is suitable for the invention, preferably 1 h.

In the embodiment of the invention, the heating extraction times in the process of preparing the ginseng water extract is 3 times, and all the extraction times of 2-3 are suitable for the invention.

5. Condensing and Drying

Combining the first, second and third extraction liquids obtained from three times of filtration, placing in a rotary evaporator, and then carrying out condensing by evaporation at the temperature of 80° C. to obtained the extractum with the relative density of 1:1, and then drying the extractum to constant weight in the oven at the temperature of 85° C. to obtain the ginseng water extract.

The ginseng water extract is brownish-yellow powder with special smell, and good water solubility. The content of the total ginsenoside in the ginseng water extract measured by the methods national standard (Appendix B of GB/T19506-2009) is 2%.

During condensing of the ginseng water extract in the invention, both the condensing temperature of 70-95° C. and the relative density of 1.05-1.15 of the concentrated extractum are suitable for the invention; and all the drying temperatures of 70-95° C. are suitable for the invention. The content of the total ginsenoside in the ginseng water extract prepared by the method of the invention is 2-5%.

Embodiment 3 Preparing Total Ginsenoside Ginseng Root

1. The First Extraction
The same as the embodiment 1
2. The Second Extraction
The same as the embodiment 1
3. The Third Extraction
The same as the embodiment 1
4. Concentration Combining the first, second and third extraction liquids obtained from three filtrations, placing the mixture in a rotary evaporator, and then concentrating the mixture by evaporation at the temperature of 80° C. to obtained the ginseng concentrated liquid (120 ml) which is equivalent to 2.5 g crude drug (the material of ginseng)/ml of ginseng solution.

During concentration of the invention, other ginseng concentrated liquid which is equivalent to 1-3.5 g of crude drug (ie, 1-3.5 g of crude drug/ml) per ml other than 2.5 g of crude drug per ml of ginseng concentrated liquid, are suitable for the present invention.

5. Macroporous Resin Column Chromatography adding the ginseng concentrated liquid into a macroporous resin column for separation, wherein the macroporous adsorption resin is D101 macroporous adsorption resin; and the proportion of the volume (300 ml) of resin in the resin column to the weight (dry weight) of the ginseng is 1:1 (which is to say when the dry weight of the ginseng is 1 kg, the volume of the macroporous resin is 1 L; and when the dry weight of the medicinal material is 1 g, the volume of the macroporous resin is 1 ml). Carrying out elution by water with the volume 4 times that of the column after the concentrated supernate flows into the resin column completely, and discarding the eluent; carrying out elution by using the ethanol solution (50%, v/v) with the volume 8 times that of the column, and collecting the eluent to obtain ginseng-macroporous resin eluent.

In the process of the macroporous resin column chromatography on the ginseng concentrated liquid, the proportion of the weight of the ginseng (crude drug) of the ginseng extraction liquid to the volume of the macroporous resin is 1:0.8-2.5 which is suitable for the invention; other kinds of macroporous adsorption resin X-5, AB-8, NK-2, NKA-2, NK-9, D3520, D101 and WLD besides D101 are suitable for the invention; during water elution, the proportion of the weight of the water to the column volume of the macroporous resin column is 2-4:1 which is suitable for the invention; when elution with the ethanol solution, all the other volume percentage concentrations of 30%-50%, besides 50%, of the ethanol solution are suitable for the invention; and the volume rate of the ethanol solution to the macroporous resin is 2-4:1 which is suitable for the invention.

6. Condensing and Drying

Putting the ginseng-macroporous resin eluent into the rotary evaporator, and under vacuum conditions, condensing at the temperature of 80° C., recycling the solvent, putting the residues into a drying oven, and drying at the temperature of 85° C. to obtain 2.6 g of the total ginsenosideginseng root.

The total ginsenoside ginseng root is brownish-yellow powder, with special smell. The content of the obtained total ginsenoside in the total ginsenoside ginseng root is 32% measured by methods in Appendix B of GB/T19506-2009.

During the process of condensing the ginseng-macroporous resin eluent in the invention, all the condensing temperatures of 65-90° C. are suitable for the invention; all the drying temperatures of 70-90° C. are suitable for the invention. The content of the total ginsenoside prepared by the method of the invention is 20-50%.

Embodiment 4 Preparing Panaxdiol Type Ginsenoside

1. The First Extraction
The same as the embodiment 3
2. The Second Extraction
The same as the embodiment 3
3. The Third Extraction
The same as the embodiment 3
4. Concentration
The same as the embodiment 3
5. The First Macroporous Resin Column Chromatography
The same as the embodiment 3, to obtain the first ginseng-resin eluent.

adding the ginseng concentrated liquid into a macroporous resin column for separation, wherein the macroporous adsorption resin is D101 macroporous adsorption resin; and the proportion of the volume (300 ml) of resin in the resin column to the weight (dry weight) of the ginseng is 1:1 (which is to say when the dry weight of the ginseng is 1 kg, the volume of the macroporous resin is 1 L; and when the dry weight of the medicinal material is 1 g, the volume of the macroporous resin is 1 ml). Carrying out elution by water with the volume 4 times that of the column after the concentrated supernate flows into the resin column completely, and discarding the eluent; carrying out elution by using the ethanol solution (50%, v/v) with the volume 8 times that of the column, and collecting the eluent to obtain the first ginseng-macroporous resin eluent.

6. The Second Macroporous Resin Column Chromatography adding the first ginseng-resin eluent into the rotary evaporator, and carrying out condensing at the temperature of 80° C. to obtain the first ginseng-macroporous resin concentrated liquid (60 ml), corresponding to 5.0 g crude drug/ml of ginseng solution.

adding the first ginseng-macroporous resin concentrated liquid sample into the macroporous resin column for separation, wherein the macroporous adsorption resin is HPD-100 macroporous adsorption resin; and the rate of the volume of the resin (300 ml) in the resin column to the weight (dry weight) of the ginseng is 1:1 (which is to say when the dry weight of the ginseng (crude drug) is 1 kg, the volume of the macroporous resin is 1 L; and when the dry weight of the medicinal material (Panax ginseng C. A. Mey.) is 1 g, the volume of the macroporous resin is 1 ml). Carrying out elution by using the ethanol solution (60%, v/v) with the volume 4 times that of the column after the concentrated supernate flows into the resin column completely, and discarding the eluent; and carrying out elution by using the ethanol solution (80%, v/v) with the volume 8 times that of the column, and collecting the eluent to obtain the second ginseng-macroporous resin eluent.

During concentration of the invention, other concentrations of the first ginseng-macroporous resin concentrated liquid is equivalent to 3.5-6 g of crude drug (ie, 3.5-6 g of crude drug/ml) per ml other than 5.0 g of crude drug per ml of the first ginseng-macroporous resin concentrated liquid, and suitable for the present invention.

In the process of the macroporous resin column chromatography on the first ginseng-macroporous resin concentrated liquid, the proportion of the weight of the ginseng (crude drug) of the first ginseng-macroporous resin concentrated liquid to the volume of the macroporous resin is 1:0.8-2.5 which is suitable for the invention; other kinds of macroporous adsorption resin HPD-200, D203 and XAD-4 besides HPD-100 are suitable for the invention; in the elution process of a 60% ethanol solution, the volume rate of the ethanol solution (60%, v/v) to the macroporous resin is 2-4:1 which is suitable for the invention; and in the elution process of a 80% ethanol solution, the volume rate of the ethanol solution (60%, v/v) to the macroporous resin is 2-4:1 which is suitable for the invention.

7. Condensing and Drying

Putting the second ginseng-macroporous resin eluent into the rotary evaporator, and under vacuum conditions, carrying out condensing at the temperature of 80° C., recycling the solvent, putting the residues into a drying oven, and carrying out drying treatment at the temperature of 85° C. to obtain 0.7 g of panaxdiol type total ginsenosides.

The panaxdiol type total ginsenosides is light yellow powder, with special smell, and good water solubility. The content of the obtained panaxdiol type ginsenoside is measured by high performance liquid chromatography according to the Appendix VI of Chinese Pharmacopoeia I (2010 version). The content of the panaxdiol type ginsenoside is 59%.

During the process of concentration of the ginseng-macroporous resin eluent in the invention, all the concentration temperatures of 65-95° C. are suitable for the invention; and all the drying temperatures of 70-95° C. are suitable for the invention. The content of the panaxadiol saponin (PDS) in the panaxdiol type ginsenoside prepared by the method of the invention is 30-70%.

Embodiment 5 Ginseng Alcohol Extract Tablet

1. Preparing raw materials according to the following mass ratio:

| | |
|---|---|
| *Ginseng* alcohol extract (the content of the total ginsenoside is 2%) | 500 g |
| Starch | 1,000 g |
| Talcum powder | 15 g |
| Magnesium stearate | 15 g |

2. Mixing the ginseng alcohol extract and the starch evenly, then preparing the mixture into granules, adding the talcum powder and the magnesium stearate, mixing uniformly, and then compressing the mixture into 10,000 tablets.

Embodiment 6 Ginseng Alcohol Extract Tablet

1. Preparing raw materials according to the following mass ratio:

| | |
|---|---|
| *Ginseng* alcohol extract (the content of the total ginsenoside is 5%) | 100 g |
| Starch | 1,000 g |
| Talcum powder | 11 g |
| Magnesium stearate | 11 g |

2. Mixing the ginseng alcohol extract and the starch uniformly, then preparing the mixture into granules, adding the talcum powder and the magnesium stearate, mixing uniformly, and then compressing the mixture into 10,000 tablets.

Embodiment 7 Ginseng Alcohol Extract Tablet

1. Preparing raw materials according to the following mass ratio:

| | |
|---|---|
| *Ginseng* alcohol extract (the content of the total ginsenoside is 3%) | 10 g |
| Starch | 1,000 g |
| Talcum powder | 10 g |
| Magnesium stearate | 10 g |

2. Mixing the ginseng alcohol extract and the starch evenly, then preparing the mixture into granules, adding the talcum powder and the magnesium stearate, mixing uniformly, and then compressing the mixture into 10,000 tablets.

Embodiment 8 Ginseng Alcohol Extract Capsule

1. Preparing raw materials according to the following mass ratio:

| | |
|---|---|
| *Ginseng* alcohol extract (the content of the total ginsenoside is 3%) | 30 g |
| Radix Sophorae Tonkinensis extract | 30 g |
| Vitamin C | 600 g |
| Starch | 1,000 g |

2. Mixing the ginseng alcohol extract, Radix Sophorae Tonkinensis extract, the vitamin C and the starch, and then feeding the mixture into capsules to form 10,000 capsules.

Embodiment 9 Ginseng Alcohol Extract Granules

1. Preparing raw materials according to the following weight proportions:

| | |
|---|---:|
| *Ginseng* alcohol extract (the content of the total ginsenoside is 3%) | 30 g |
| *Zingiber officinale* Rosc. extract | 30 g |
| Vitamin C | 600 g |
| Sucrose powder | 5,000 g |

2. Mixing the ginseng alcohol extract, the *Zingiber officinale* Rosc. extract, the vitamin C and the Sucrose powder uniformly, preparing the mixture into granules, and then feeding the granules into bags to form 10,000 bags.

Embodiment 10 Ginseng Alcohol Extract Oral Liquid

1. Preparing raw materials according to the following mass ratio:

| | |
|---|---:|
| *Ginseng* alcohol extract (the content of the total ginsenoside is 3%) | 4 g |
| Herba Herba *Scutellariae barbatae* extract | 3 g |
| Radix *Sophorae flavescentis* extract | 3 g |
| Glucose syrup | 5 g |
| Deionized water | appropriate |

2. Dissolving the ginseng alcohol extract by using a small amount of ethanol, adding the Herba Scutellariae barbatae extract, the Radix Sophorae flavescentis extract and the glucose syrup into the solution, and finally adding the deionized water to 100 ml to obtain the ginseng alcohol extract oral liquid.

Embodiment 11 Ginseng Water Extract Tablet

1. Preparing raw materials according to the following mass ratio:

| | |
|---|---:|
| *Ginseng* water extract (the content of the total ginsenoside is 2%) | 500 g |
| Starch | 1,000 g |
| Talcum powder | 15 g |
| Magnesium stearate | 15 g |

2. Mixing the ginseng water extract and the starch evenly, then preparing the mixture into granules, adding the talcum powder and the magnesium stearate, mixing uniformly, and then compressing the mixture into 10,000 tablets.

Embodiment 12 Ginseng Water Extract Tablet

1. Preparing raw materials according to the following mass ratio:

| | |
|---|---:|
| *Ginseng* water extract (the content of the total ginsenoside is 3%) | 100 g |
| Starch | 1,000 g |
| Talcum powder | 11 g |
| Magnesium stearate | 11 g |

2. Mixing the ginseng water extract and the starch evenly, then preparing the mixture into granules, adding the talcum powder and the magnesium stearate, mixing uniformly, and then compressing the mixture into 10,000 tablets.

Embodiment 13 Ginseng Water Extract Tablet

1. Preparing raw materials according to the following mass ratio:

| | |
|---|---:|
| *Ginseng* water extract (the content of the total ginsenoside is 5%) | 10 g |
| Starch | 1,000 g |
| Talcum powder | 10 g |
| Magnesium stearate | 10 g |

2. Mixing the ginseng water extract and the starch evenly, then preparing the mixture into granules, adding the talcum powder and the magnesium stearate, mixing uniformly, and then compressing the mixture into 10,000 tablets.

Embodiment 14 Ginseng Water Extract Capsule

1. Preparing raw materials according to the following mass ratio:

| | |
|---|---:|
| *Ginseng* alcohol extract (the content of the total ginsenoside is 3%) | 30 g |
| Radix Sophorae Tonkinensis extract | 30 g |
| Vitamin C | 600 g |
| Starch | 1,000 g |

2. Mixing the ginseng water extract, Radix Sophorae Tonkinensis extract, the vitamin C and the starch, and then feeding the mixture into capsules to form 10,000 capsules.

Embodiment 15 Ginseng Water Extract Granules

1. Preparing raw materials according to the following weight proportions:

| | |
|---|---:|
| Ginseng water extract (the content of the total ginsenoside is 3%) | 30 g |
| *Zingiber officinale* Rosc. extract | 30 g |
| Vitamin C | 600 g |
| Sucrose powder | 5,000 g |

2. Mixing the ginseng water extract, the *Zingiber officinale* Rosc. extract, the vitamin C and the Sucrose powder uniformly, preparing the mixture into granules, and then feeding the granules into bags to form 10,000 bags.

Embodiment 16 Ginseng Water Extract Oral Liquid

1. Preparing raw materials according to the following mass ratio:

| | |
|---|---:|
| Ginseng water extract (the content of the total ginsenoside is 3%) | 4 g |
| Herba *Scutellariae barbatae* extract | 3 g |
| Radix *Sophorae flavescentis* extract | 3 g |
| Glucose syrup | 5 g |
| Deionized water | appropriate |

2. Dissolving the ginseng water extract by using a small amount of ethanol, adding the Herba Scutellariae barbatae extract, the Radix Sophorae flavescentis extract and the glucose syrup into the solution, and finally adding the deionized water to 100 ml to obtain the ginseng water extract oral liquid.

Embodiment 17 Total Ginsenoside Ginseng Root Tablet

1. Preparing raw materials according to the following mass ratio:

| | |
|---|---:|
| Total ginsenoside ginseng root (the content of the total ginsenoside is 32%) | 500 g |

-continued

| | |
|---|---|
| Starch | 1,000 g |
| Talcum powder | 15 g |
| Magnesium stearate | 15 g |

2. Mixing the ginseng total geinsenoside and the starch evenly, then preparing the mixture into granules, adding the talcum powder and the magnesium stearate, mixing uniformly, and then compressing the mixture into 10,000 tablets.

Embodiment 18 Total Ginsenoside Ginseng Root Tablet

1. Preparing raw materials according to the following mass ratio:

| | |
|---|---|
| Total ginsenoside ginseng root (the content of the total ginsenoside is 25%) | 100 g |
| Starch | 1,000 g |
| Talcum powder | 11 g |
| Magnesium stearate | 11 g |

2. Mixing the ginseng total geinsenoside and the starch evenly, then preparing the mixture into granules, adding the talcum powder and the magnesium stearate, mixing uniformly, and then compressing the mixture into 10,000 tablets.

Embodiment 19 Total Ginsenoside Ginseng Root Tablet

1. Preparing raw materials according to the following mass ratio:

| | |
|---|---|
| Total ginsenoside ginseng root the content of the total ginsenoside is 50%) | 10 g |
| Starch | 1,000 g |
| Talcum powder | 10 g |
| Magnesium stearate | 10 g |

2. Mixing the ginseng total geinsenoside and the starch evenly, then preparing the mixture into granules, adding the talcum powder and the magnesium stearate, mixing uniformly, and then compressing the mixture into 10,000 tablets.

Embodiment 20 Total Ginsenoside Ginseng Root Capsule

1. Preparing raw materials according to the following mass ratio:

| | |
|---|---|
| Total ginsenoside ginseng root (the content of the total ginsenoside is 32%) | 30 g |
| Radix *Sophorae Tonkinensis* extract | 30 g |
| Vitamin C | 600 g |
| Starch | 1,000 g |

2. Mixing the ginseng total geinsenoside, Radix Sophorae Tonkinensis extract, the vitamin C and the starch, and then feeding the mixture into capsules to form 10,000 capsules.

Embodiment 21 Total Ginsenoside Ginseng Root Granules

1. Preparing raw materials according to the following weight proportions:

| | |
|---|---|
| Total ginsenoside ginseng root (the content of the total ginsenoside is 32%) | 30 g |
| *Zingiber officinale* Rosc. extract | 30 g |
| Vitamin C | 600 g |
| Sucrose powder | 5,000 g |

2. Mixing the ginseng total geinsenoside, the *Zingiber officinale* Rosc, extract, the vitamin C and the Sucrose powder uniformly, preparing the mixture into granules, and then feeding the granules into bags to form 10,000 bags.

Embodiment 22 Total Ginsenoside Ginseng Root Oral Liquid

1. Preparing raw materials according to the following mass ratio:

| | |
|---|---|
| Total ginsenoside ginseng root (the content of the total ginsenoside is 32%) | 4 g |
| Herba *Scutellariae barbatae* extract | 3 g |
| Radix *Sophorae flavescentis* extract | 3 g |
| Glucose syrup | 5 g |
| Deionized water | appropriate |

2. Dissolving the Ginseng total ginsenoside by using a small amount of ethanol, adding the Herba Scutellariae barbatae extract, the Radix Sophorae flavescentis extract and the glucose syrup into the solution, and finally adding the deionized water to 100 ml to obtain the total ginsenoside oral liquid.

Embodiment 23 Panaxdiol Type Ginsenoside Tablet

1. Preparing raw materials according to the following mass ratio:

| | |
|---|---|
| Panaxdiol type ginsenoside (the content of the panaxadiol saponin is 59%) | 500 g |
| Starch | 1,000 g |
| Talcum powder | 15 g |
| Magnesium stearate | 15 g |

2. Mixing the panaxdiol type ginsenoside and the starch evenly, then preparing the mixture into granules, adding the talcum powder and the magnesium stearate, mixing uniformly, and then compressing the mixture into 10,000 tablets.

Embodiment 24 Panaxdiol Type Ginsenoside Tablet

1. Preparing raw materials according to the following mass ratio:

| | |
|---|---|
| Panaxdiol type ginsenoside (the content of the panaxadiol saponin is 35%) | 100 g |
| Starch | 1,000 g |
| Talcum powder | 11 g |
| Magnesium stearate | 11 g |

2. Mixing the panaxdiol type ginsenoside and the starch evenly, then preparing the mixture into granules, adding the talcum powder and the magnesium stearate, mixing uniformly, and then compressing the mixture into 10,000 tablets.

Embodiment 25 Panaxdiol Type Ginsenoside Tablet

1. Preparing raw materials according to the following mass ratio:

| | |
|---|---|
| Panaxdiol type ginsenoside (the content of the panaxadiol saponin is 70%) | 10 g |
| Starch | 1,000 g |
| Talcum powder | 10 g |
| Magnesium stearate | 10 g |

2. Mixing the panaxdiol type ginsenoside and the starch evenly, then preparing the mixture into granules, adding the talcum powder and the magnesium stearate, mixing uniformly, and then compressing the mixture into 10,000 tablets.

Embodiment 26 Panaxdiol Type Ginsenoside Capsule

1. Preparing raw materials according to the following mass ratio:

| | |
|---|---|
| Panaxdiol type ginsenoside (the content of the panaxadiol saponin is 59%) | 30 g |
| Radix *Sophorae Tonkinensis* extract | 30 g |
| Vitamin C | 600 g |
| Starch | 1,000 g |

2. Mixing the panaxdiol type ginsenoside, Radix Sophorae Tonkinensis extract, the vitamin C and the starch, and then feeding the mixture into capsules to form 10,000 capsules.

Embodiment 27 Panaxdiol Type Ginsenoside Granules

1. Preparing raw materials according to the following mass ratio:

| | |
|---|---|
| Panaxdiol type ginsenoside (the content of the panaxadiol saponin is 59%) | 30 g |
| *Zingiber officinale* Rosc. extract | 30 g |
| Vitamin C | 600 g |
| Sucrose powder | 5,000 g |

2. Mixing the panaxdiol type ginsenoside, the *Zingiber officinale* Rosc. extract, the vitamin C and the Sucrose powder evenly, preparing the mixture into granules, and then feeding the granules into bags to form 10,000 bags.

Embodiment 28 Panaxdiol Type Ginsenoside Oral Liquid

1. Preparing raw materials according to the following mass ratio:

| | |
|---|---|
| Panaxdiol type ginsenoside (the content of the panaxadiol saponin is 59%) | 4 g |
| Herba *Scutellariae barbatae* extract | 3 g |
| Radix *Sophorae flavescentis* extract | 3 g |
| Glucose syrup | 5 g |
| Deionized water | appropriate |

2. Dissolving the panaxdiol type ginsenoside by using a small amount of ethanol, adding the Herba Scutellariae barbatae extract, the Radix Sophorae flavescentis extract and the glucose syrup into the solution, and finally adding the deionized water to 100 ml to obtain the panaxdiol type ginsenoside oral liquid.

Embodiment 29 Ginsenoside rg3 Tablet

1. Preparing raw materials according to the following mass ratio:

| | |
|---|---|
| 20(R)-Ginsenoside rg3 (content of 60%) | 500 g |
| Starch | 1,000 g |
| Talcum powder | 15 g |
| Magnesium stearate | 15 g |

2. Mixing the Ginsenoside rg3 and the starch evenly, then preparing the mixture into granules, adding the talcum powder and the magnesium stearate, mixing uniformly, and then compressing the mixture into 10,000 tablets.

Embodiment 30 Ginsenoside rg3 Tablet

1. Preparing raw materials according to the following mass ratio:

| | |
|---|---|
| 20(R)-Ginsenoside rg3 (98%) | 100 g |
| Starch | 1,000 g |
| Talcum powder | 11 g |
| Magnesium stearate | 11 g |

2. Mixing the Ginsenoside rg3 and the starch evenly, then preparing the mixture into granules, adding the talcum powder and the magnesium stearate, mixing uniformly, and then compressing the mixture into 10,000 tablets.

Embodiment 31 Ginsenoside rg3 Tablet

1. Preparing raw materials according to the following mass ratio:

| | |
|---|---|
| 20(R)-Ginsenoside rg3 (98%) | 10 g |
| Starch | 1,000 g |
| Talcum powder | 10 g |
| Magnesium stearate | 10 g |

2. Mixing the Ginsenoside rg3 and the starch evenly, then preparing the mixture into granules, adding the talcum powder and the magnesium stearate, mixing uniformly, and then compressing the mixture into 10,000 tablets.

Embodiment 32 Ginsenoside rg3 Capsule

1. Preparing raw materials according to the following mass ratio:

| | |
|---|---|
| 20(R)-Ginsenoside rg3 (with the content of 98%) | 30 g |
| Radix *Sophorae Tonkinensis* extract | 30 g |
| Vitamin C | 600 g |
| Starch | 1,000 g |

2. Mixing the Ginsenoside rg3, Radix Sophorae Tonkinensis extract, the vitamin C and the starch, and then feeding the mixture into capsules to form 10,000 capsules.

Embodiment 33 Ginsenoside rg3 Granules

1. Preparing raw materials according to the following weight proportions:

| | |
|---|---|
| 20(R)-Ginsenoside rg3 (with the content of 98%) | 30 g |
| *Zingiber officinale* Rosc. extract | 30 g |
| Vitamin C | 600 g |
| Sucrose powder | 5,000 g |

2. Mixing the ginsenoside rg3, the *Zingiber officinale* Rosc. extract, the vitamin C and the Sucrose powder uniformly, preparing the mixture into granules, and then feeding the granules into bags to form 10,000 bags.

Embodiment 34 Ginsenoside rg3 Oral Liquid

1. Preparing raw materials according to the following mass ratio:

| | |
|---|---|
| 20(R)-Ginsenoside rg3 (with the content of 98%) | 4 g |
| Herba *Scutellariae barbatae* extract | 3 g |
| Radix *Sophorae flavescentis* extract | 3 g |
| Glucose syrup | 5 g |
| Deionized water | appropriate |

2. Dissolving the ginsenoside rg3 by using a small amount of ethanol, adding the Herba Scutellariae barbatae extract, the Radix Sophorae flavescentis extract and the glucose syrup into the solution, and finally adding the deionized water to 100 ml to obtain the ginsenoside rg3 oral liquid.

Embodiment 35 Ginsenoside rg3 Derivative (20(R)-Ginsenoside Rg3 8-N-Butyrate) Tablet 1. Preparing raw materials according to the following mass ratio:

| Ginsenoside rg3 derivative (with the content of 60%) | 500 g |
| Starch | 1,000 g |
| Talcum powder | 15 g |
| Magnesium stearate | 15 g |

2. Mixing the Ginsenoside rg3 derivative and the starch evenly, then preparing the mixture into granules, adding the talcum powder and the magnesium stearate, mixing uniformly, and then compressing the mixture into 10,000 tablets.

Embodiment 36 Ginsenoside rg3 Derivative (20(R)-Ginsenoside Rg3 8-N-Butyrate) Tablet 1. Preparing raw materials according to the following mass ratio:

| Ginsenoside rg3 derivative (with the content of 98%) | 100 g |
| Starch | 1,000 g |
| Talcum powder | 11 g |
| Magnesium stearate | 11 g |

2. Mixing the Ginsenoside rg3 derivative and the starch evenly, then preparing the mixture into granules, adding the talcum powder and the magnesium stearate, mixing uniformly, and then compressing the mixture into 10,000 tablets.

Embodiment 37 Ginsenoside rg3 Derivative (20(R)-Ginsenoside Rg3 8-N-Butyrate) Tablet 1. Preparing raw materials according to the following mass ratio:

| Ginsenoside rg3 derivative (with the content of 98%) | 10 g |
| Starch | 1,000 g |
| Talcum powder | 10 g |
| Magnesium stearate | 10 g |

2. Mixing the Ginsenoside rg3 derivative and the starch evenly, then preparing the mixture into granules, adding the talcum powder and the magnesium stearate, mixing uniformly, and then compressing the mixture into 10,000 tablets.

Embodiment 38 Ginsenoside rg3 Derivative (20(R)-ginsenoside Rg3 8-N-Butyrate) Capsule 1. Preparing raw materials according to the following mass ratio:

| Ginsenoside rg3 derivative (with the content of 98%) | 30 g |
| Radix Sophorae Tonkinensis extract | 30 g |
| Vitamin C | 600 g |
| Starch | 1,000 g |

2. Mixing the Ginsenoside rg3 derivative, Radix Sophorae Tonkinensis extract, the vitamin C and the starch, and then feeding the mixture into capsules to form 10,000 capsules.

Embodiment 39 Ginsenoside rg3 Derivative (20(R)-Ginsenoside Rg3 8-N-Butyrate) Granules 1. Preparing raw materials according to the following weight proportions:

| Ginsenoside rg3 derivative (with the content of 98%) | 30 g |
| *Zingiber officinale* Rosc. extract | 30 g |
| Vitamin C | 600 g |
| Sucrose powder | 5,000 g |

2. Mixing the ginsenoside rg3 derivative, the *Zingiber officinale* Rosc. extract, the vitamin C and the Sucrose powder uniformly, preparing the mixture into granules, and then feeding the granules into bags to form 10,000 bags.

Embodiment 40 Ginsenoside rg3 Derivative (20(R)-Ginsenoside Rg3 8-N-Butyrate) Oral Liquid 1. Preparing raw materials according to the following mass ratio:

| Ginsenoside rg3 derivative (with the content of 98%) | 4 g |
| Herba *Scuteliariae barbatae* extract | 3 g |
| Radix *Sophorae flavescentis* extract | 3 g |
| Glucose syrup | 5 g |

2. Dissolving the ginsenoside rg3 derivative by using a small amount of ethanol, adding the Herba Scutellariae barbatae extract, the Radix Sophorae flavescentis extract and the glucose syrup into the solution, and finally adding the deionized water to 100 ml to obtain the ginsenoside rg3 derivative oral liquid.

Test Example 1 Effects of Ginseng extract, Ginsenoside and Derivatives on Immune Functions in Mice with HCMV Infection 1. Experimental Materials 1.1 Animals, Viruses and Cells Kunming mice (weight: 18-22 g), half male and half female, provided by the Animal Center of Zhejiang Chinese Medical University, license number of SCXK (Shanghai) 2008-0016.

Viruses and cells: HCMVADI69 standard strains and human embryonic lung fibroblasts (HEL) which are provided by Viral Laboratory of Shandong Academy of Medical Sciences.

Human cytomegalovirus monoclonal antibodies (HCM-VMcAb) are introduced from Diagnosis Room of Virus Institute in Chinese Academy of Preventive Medicine, and are early antigen monoclonal antibodies. ELISA (enzyme-linked immunosorbent assay) is used with the working titer of $1\times10^{-5}$.

1.2 Drugs

Ginseng alcohol extracts: brownish-yellow powder, containing 3% of the total ginsenoside, produced by Dalian Fusheng Natural Medicine Development Co., Ltd., with the batch number of 20120601;

Ginseng water extracts: brownish-yellow powder, containing 2% of the total ginsenoside, produced by Dalian Fusheng Natural Medicine Development Co., Ltd., with the batch number of 20120602;

Total ginsenoside ginseng root: brownish-yellow powder containing 32% of the total ginsenoside, produced by Dalian Fusheng Natural Medicine Development Co., Ltd., with the batch number of 20120502;

Panaxdiol type ginsenoside: light yellow powder, containing 59% of panaxadiol saponin (PDS), produced by Dalian Fusheng Natural Medicine Development Co., Ltd., with the batch number of 20120403;

20(R)-ginsenoside Rg3 (content: >98%) is produced by Dalian Fusheng Natural Medicine Development Co., Ltd., with the batch number of 20120303;by comparison with a standard product provided by National Institute for Food and Drug Control of China and by measured by HPLC, the content accords with the calibration value, and the measured value is 98.2%;

Ginsenoside Rg3 derivatives (20(R)-ginsenoside Rg3 8-N-butyrate) are developed by Dalian Fusheng Natural Medicine Development Co., Ltd., and measured by an area normalization method through two detectors for HPLC, namely an UV detector and an evaporative light-scattering detector, respectively with the purity of 99.6%.

Positive control drug: ganciclovir (specification: 250 mg; Lizhu Group Hubei Keyi Pharmaceutical Co., Ltd.; batch number: 020506), the clinical daily dose of 45.5 mg/kg body weight.

1.3 Virus standard strain HCMVADI69 and the proliferation of species are introduced in October 1999 from Virus Seed Room of Virus Institute in Chinese Academy of Preventive Medicine. The virus was dissolved in 1640 culture medium and inoculated on standby single-layer HEL cells; lesions of the cells occur and are swelled at 37° C. after 16 h; refraction particles in cytoplasm are increased; parts of cells are rounded; and individual cells fall off. With the extension of inoculating time, the range of the lesion was expanded to reach more than 90% of the lesion when cultured for 96 hours. HEL cultural supernatant reaching +++−++++ in the cell lesions is discarded and lightly washed for 3 times by PBS; double distilled water is added; freeze-thawing is performed for 3 times at −20° C.; vigorous blowing and beating are performed; 10,000 r/min centrifugation is performed at 4° C. for 20 min; and the supernatant is collected to obtain the standard virus strain.

2. Experimental Method 2.1 Grouping and Administration

210 Kunming mice, male and female in half, are feeded for 1 week under experiment conditions, and divided into 21 groups at random by gender and body mass: a normal control group; a model group; a positive drug control group; high/medium/low-dose ginseng alcohol extract groups; high/medium/low-dose ginseng water extract groups; high/medium/low-dose total ginsenoside ginseng root groups; high/medium/low-dose panaxdiol type ginsenoside groups; high/medium/low-dose ginsenoside rg3 groups; and high/medium/low-dose ginsenoside rg3 derivative groups.

Ganciclovir (45.5 mg/kg/d) is given to the positive control group; the ginseng alcohol extracts 0.012 mg/kg/d, 0.06 mg/kg/d and 0.3 mg/kg/d are given to the three groups of the ginseng alcohol extracts respectively; the ginseng water extracts 0.012 mg/kg/d, 0.06 mg/kg/d and 0.3 mg/kg/d are given to the three groups of the ginseng water extracts respectively; the ginseng total ginsenoside 0.012 mg/kg/d, 0.06 mg/kg/d and 0.3 mg/kg/d are given to the three groups of the total ginsenoside ginseng root respectively; the panaxdiol type ginsenoside 0.012 mg/kg/d, 0.06 mg/kg/d and 0.3 mg/kg/d are given to the three groups of the panaxdiol type ginsenoside respectively; the ginsenoside rg3 0.012 mg/kg/d, 0.06 mg/kg/d and 0.3 mg/kg/d are given to the three groups of the ginsenoside rg3 respectively; the ginsenoside rg3 derivatives 0.012 mg/kg/d, 0.06 mg/kg/d and 0.3 mg/kg/d are given to the three groups of the ginsenoside rg3 derivatives respectively.

The mice were injected with HCMV$10^{-3}$ (0.1 ml/mouse) through the caudal vein of mouse tails; 0.9% normal saline is injected to the normal control group, 0.1 ml/piece; and intragastric administration is started according to the determined dosage on the second day of infection, with 21 days of medication.

2.2 Determination of Weight, Thymus Index and Spleen Index

During the experiment. Animals were weighed and the thymus and spleen were weighed on the $21^{st}$ day of administration, and their indices (thymus index, spleen index, weight of thymus and spleen organs per 10 g body weight (mg)) were measured.

2.3 Determination of Serum Hemolysin Antibodies 40 min later after the last administration, picking eyeballs to take blood, collecting serum, diluting the serum for 100 times with normal saline, uniformly mixing 1 mL of the diluted serum, 0.5 mL of 5% chicken erythrocyte suspension and 0.5 mL of 10% complement (guinea pig serum), incubating for 30 min In 37° C. incubator, setting 0° C. refrigerator for 30 min to stop the reaction. Centrifugating, taking the supernatant, and then measuring the optical density (OD value) at 540 nm by spectrophotometer.

2.4 Determination of IL-2 Level in Serum

Selecting six mice in each group randomly for sampling, 40 min later after the last administration, picking eyeballs to take blood, and collecting the blood by a centrifugal tube Performing high-speed centrifugation for 5 min at 3000 r/min after blood coagulation, and taking the serum. The IL-2 in the serum is measured according to the manual of an ELISA kit.

3. Experimental Results 3.1 Determination of Survival Rate and Weight of HCMV Infected Mice Recording the number of dead animals in the experimental process. The test results of the survival rate and the weight of HCMV infected mice are shown in Table 1.

All the mice are subjected to the medicines continuously for 21 days in the whole experimental process. During administration, piloerection, hemiplegia, whole-body ataxia and weight reduction and other infection-toxic symptoms occur in the mice of the model group at the earliest 2-4 d later after exposure to toxicant, death starts to occur 5-7 d later, and only 3 mice survive until 21 d, which indicates successful modeling.

The mice from the groups of the ginseng alcohol extracts, the ginseng water extracts, the total ginsenoside ginseng root, the panaxdiol type ginsenoside, the 20(R)-ginsenoside Rg3 and the 20(R)-ginsenoside Rg3 derivatives having a mild toxic symptom, less death and good weight growth, which indicated that these drugs have a certain inhibitory effect on the viruses and can increase the survival rate of the mice to varying degrees. The number of surviving animals in all the groups were respectively compared with that of the model group statistically, which proves remarkable differences of high-dosage groups as well as a certain protection effect of medium/low-dosage groups on the HCMV infected mice. The survival number, weight growth and symptom expression of ganciclovir animals are totally approximate to those of the large-dosage groups.

TABLE 1

Influences of Ginseng Extracts and Derivatives onWeight of HCMV Infected Mice Thereof (X ± S)

| Groups | | Animal number (n) Before infection | Animal number (n) Termination of treatment | Average animal weight (g) Before treatment | Average animal weight (g) Termination of treatment |
|---|---|---|---|---|---|
| Normal control group | | 10 | 10 | 20.8 ± 2.10 | 30.4 ± 7.00 |
| Model group | | 10 | 3 | 21.8 ± 1.72 | 19.5 ± 3.38 |
| Positive drug control group | | 10 | 8 | 20.2 ± 1.12 | 26.9 ± 3.97 |
| Ginseng alcohol extracts | Low-dosage group | 10 | 4 | 20.1 ± 0.98 | 19.8 ± 2.99 |
| | Medium-dosage group | 10 | 4 | 20.8 ± 0.64 | 20.5 ± 0.82 |
| | High-dosage group | 10 | 5 | 20.6 ± 1.26 | 21.4 ± 2.15 |
| Ginseng water extracts | Low-dosage group | 10 | 4 | 21.1 ± 0.57 | 21.7 ± 0.28 |
| | Medium-dosage group | 10 | 4 | 20.2 ± 0.19 | 22.4 ± 0.52 |
| | High dosage group | 10 | 5 | 21.6 ± 2.02 | 22.8 ± 1.06 |
| total ginsenoside ginseng root | Low-dosage group | 10 | 5 | 20.3 ± 0.88 | 23.0 ± 0.51 |
| | Medium-dosage group | 10 | 5 | 21.4 ± 0.09 | 23.4 ± 0.80 |
| | High dosage group | 10 | 7 | 19.8 ± 1.66 | 23.9 ± 0.71 |
| Panaxdiol type ginsenoside | Low-dosage group | 10 | 6 | 20.2 ± 2.31 | 24.1 ± 0.88 |
| | Medium-dosage group | 10 | 6 | 19.8 ± 1.84 | 24.2 ± 0.76 |
| | High-dosage group | 10 | 7 | 21.0 ± 1.08 | 24.7 ± 0.82 |
| Ginsenoside rg3 | Low-dosage group | 10 | 6 | 22.6 ± 2.04 | 25.1 ± 0.11 |
| | Medium-dosage group | 10 | 6 | 19.6 ± 1.32 | 25.8 ± 0.54 |
| | High-dosage group | 10 | 8 | 20.5 ± 0.51 | 26.6 ± 1.83 |
| Ginsenoside rg3 derivatives | Low-dosage group | 10 | 6 | 20.9 ± 0.43 | 26.4 ± 0.18 |
| | Medium-dosage group | 10 | 7 | 20.3 ± 1.47 | 27.1 ± 0.49 |
| | High-dosage group | 10 | 9 | 20.2 ± 0.95 | 27.7 ± 1.84 |

3.2 Influences on Spleen and Thymus Gland Indexes of HCMV Infected Mice

Thymus glands and spleens are important immune organs, with the organ indexes reflecting the strength of immune functions of organisms to a certain degree. The thymus glands have the main functions of generating T-lymphocytes and secreting thymosin, and mainly take part in cellular immunity; and abundant lymphocytes and macrophages are contained in the spleens. The weight of the thymus glands and the spleens is related to functions thereof as well as the quantity of immune cells therein, and the height depends on the proliferation degree of the lymphocytes therein. The results of spleen and thymus gland indexes of the experiment are shown in Table 2.

TABLE 2

Comparison of Influences of Ginseng Extracts and Derivatives Thereof on Spleen and Thymus Gland Indexes of HCMV Infected Mice (X ± S)

| Groups | | Number of animals after termination of treatment | Spleen indexes | Thymus gland indexes |
|---|---|---|---|---|
| Normal control group | | 10 | 0.065 ± 0.023 | 0.036 ± 0.011 |
| Model group | | 3 | 0.049 ± 0.034 | 0.019 ± 0.034 |
| Positive drug control group | | 8 | 0.058 ± 0.017 | 0.023 ± 0.008 |
| Ginseng alcohol extracts | Low-dosage group | 4 | 0.051 ± 0.032 | 0.021 ± 0.025 |
| | Medium-dosage group | 4 | 0.053 ± 0.009 | 0.021 ± 0.024 |
| | High-dosage group | 5 | 0.053 ± 0.011 | 0.023 ± 0.009 |
| Ginseng water extracts | Low-dosage group | 4 | 0.052 ± 0.005 | 0.022 ± 0.026 |
| | Medium-dosage group | 4 | 0.052 ± 0.039 | 0.024 ± 0.043 |
| | High-dosage group | 5 | 0.053 ± 0.041 | 0.024 ± 0.020 |
| total ginsenoside ginseng root | Low-dosage group | 5 | 0.052 ± 0.030 | 0.024 ± 0.014 |
| | Medium-dosage group | 5 | 0.054 ± 0.044 | 0.025 ± 0.009 |
| | High-dosage group | 7 | 0.055 ± 0.012 | 0.027 ± 0.018 |
| Panaxdiol type ginsenoside | Low-dosage group | 6 | 0.055 ± 0.026 | 0.025 ± 0.007 |
| | Medium-dosage group | 6 | 0.055 ± 0.029 | 0.025 ± 0.016 |
| | High-dosage group | 7 | 0.057 ± 0.018 | 0.027 ± 0.023 |
| Ginsenoside rg3 | Low-dosage group | 6 | 0.056 ± 0.045 | 0.027 ± 0.011 |
| | Medium-dosage group | 6 | 0.057 ± 0.013 | 0.029 ± 0.021 |
| | High-dosage group | 8 | 0.061 ± 0.021 | 0.031 ± 0.009 |
| Ginsenoside rg3 derivatives | Low-dosage group | 6 | 0.059 ± 0.036 | 0.027 ± 0.006 |
| | Medium-dosage group | 7 | 0.061 ± 0.027 | 0.029 ± 0.008 |
| | High-dosage group | 9 | 0.062 ± 0.032 | 0.032 ± 0.017 |

The experiment proves that the ginseng alcohol extracts, the ginseng water extracts, the ginseng total ginsenoside, the panaxdiol type ginsenoside, the ginsenoside rg3 and the ginsenoside rg3 derivatives have an obvious weight increasing effect on the immune organs of the HCMV infected mice, the weight of all the experimental groups is higher than that of the model group, and particularly, the spleen indexes and the thymus gland indexes of the ginsenoside rg3 and ginsenoside rg3 derivative groups were significantly different from those of the model group respectively. The experimental results state that the ginseng extracts, the ginsenoside and the derivatives thereof can achieve a protection effect on the thymus glands and the spleens of the HCMV infected mice, have an immune effect similar to that of antigens, can recover and promote the activity of splenic lymphocytes and have a positive immune regulation effect. Therefore, the ginseng extracts and the derivatives thereof can be used for treating the HCMV infection.

3.3 Experimental Results of IL-2 Level in Serum 1L-2, namely interleukin-2, is also named T cell growth factor (TCGF), is a cell factor with wide biological activity, which is generated by activated CD4+Th1 cells, and can promote the proliferation of Th0 and CTL, thus being an important factor for regulating and controlling immune responses. The IL-2 has a multicell source (mainly generated by activated T cells) as well as cell factors (mainly used for promoting growth, proliferation and differentiation of the lymphocytes) with a pleiotropic action; have an important effect on the immune responses and anti-virus infection and the like of the organisms, and can stimulate T cell proliferation started by specific antigens or mitogenic factors; can activate the T cells and promote the generation of the cell factors; stimulate NK cell proliferation, enhance NK killing activity and generate the cell factors to induce the generation of LAK cells; promote the proliferation and antibody production of B cells; and activate macrophages. The experimental results of the IL-2 level in the mice serum are shown in Table 3.

TABLE 3

Results of IL-2 Concentration in Serum of HCMV Infected Mice (X ± S)

| Groups | | Number of animals after termination of treatment | IL-2 concentration (pg/ml) |
|---|---|---|---|
| Normal control group | | 10 | 34.45 ± 3.99 |
| Model group | | 3 | 21.18 ± 6.24 |
| Positive drug control group | | 8 | 24.54 ± 2.66 |
| Ginseng alcohol extracts | Low-dosage group | 4 | 23.94 ± 3.21 |
| | Medium-dosage group | 4 | 23.98 ± 2.55 |
| | High-dosage group | 5 | 24.07 ± 3.94 |
| Ginseng water extracts | Low-dosage group | 4 | 24.12 ± 3.22 |
| | Medium-dosage group | 4 | 24.35 ± 4.69 |
| | High-dosage group | 5 | 26.02 ± 3.17 |
| total ginsenoside ginseng root | Low-dosage group | 5 | 25.62 ± 4.04 |
| | Medium-dosage group | 5 | 25.11 ± 3.05 |
| | High-dosage group | 7 | 26.92 ± 6.05 |
| Panaxdiol type ginsenoside | Low dosage group | 6 | 25.62 ± 2.69 |
| | Medium-dosage group | 6 | 25.93 ± 3.06 |
| | High-dosage group | 7 | 27.11 ± 2.62 |
| Ginsenoside rg3 | Low-dosage group | 6 | 27.02 ± 6.39 |
| | Medium-dosage group | 6 | 27.19 ± 5.60 |
| | High-dosage group | 8 | 28.64 ± 4.66 |
| Ginsenoside rg3 derivatives | Low-dosage group | 6 | 27.99 ± 5.38 |
| | Medium-dosage group | 7 | 28.62 ± 4.21 |
| | High-dosage group | 9 | 29.32 ± 4.09 |

The results of table 3 show that: the model group has the lowest level of IL-2, which is significantly different from the normal control group (P<0.01), indicating that the model is successful. The of IL-2 in the group of ginseng alcohol extracts, the ginseng water extracts, the total ginsenoside, the panaxdiol type ginsenoside, the ginsenoside rg3 and the ginsenoside rg3 derivatives are higher than those of the model group, which indicates that the ginseng alcohol extracts, the ginseng water extracts, the total ginsenoside, the panaxdiol type ginsenoside, the ginsenoside rg3 and the ginsenoside rg3 derivatives have the effect of enhancing the IL-2 level of the HCMV infected mice; and the IL-2 level of the ginseng water extract, ginseng total ginsenoside, panaxdiol type ginsenoside, ginsenoside rg3 and ginsenoside rg3 derivative groups are superior to that of the positive drug control group, which indicates that the ginseng water extract, total ginsenoside, panaxdiol type ginsenoside, ginsenoside rg3 and ginsenoside rg3 derivative groups have a stronger treatment effect on the HCMV infected mice than positive drugs.

3.4 Determination of Hemolysin Antibodies in Serum

The measurement results of hemolysin antibodies in the mice serum are shown in table 4.

TABLE 4

Results of Hemolysin Antibodies in Serum of HCMV Infected Mice (X ± S)

| Groups | | Number of animals after termination of treatment | Hemolysin (OD value) |
|---|---|---|---|
| Normal control group | | 10 | 0.20 ± 0.06 |
| Model group | | 3 | 0.021 ± 0.01 |
| Positive drug control group | | 8 | 0.11 ± 0.04 |
| Ginseng alcohol extracts | Low-dosage group | 4 | 0.09 ± 0.02 |
| | Medium-dosage group | 4 | 0.10 ± 0.03 |
| | High-dosage group | 5 | 0.11 ± 0.01 |
| Ginseng water extracts | Low-dosage group | 4 | 0.10 ± 0.08 |
| | Medium-dosage group | 4 | 0.11 ± 0.04 |
| | High-dosage group | 5 | 0.12 ± 0.07 |
| total ginsenoside ginseng root | Low-dosage group | 5 | 0.12 ± 0.09 |
| | Medium-dosage group | 5 | 0.13 ± 0.03 |
| | High-dosage group | 7 | 0.15 ± 0.01 |
| Panaxdiol type ginsenoside | Low-dosage group | 6 | 0.13 ± 0.09 |
| | Medium-dosage group | 6 | 0.14 ± 0.06 |
| | High dosage group | 7 | 0.16 ± 0.02 |
| Ginsenoside rg3 | Low-dosage group | 6 | 0.15 ± 0.08 |
| | Medium-dosage group | 6 | 0.16 ± 0.05 |
| | High-dosage group | 8 | 0.18 ± 0.03 |

TABLE 4-continued

Results of Hemolysin Antibodies in Serum of HCMV Infected Mice (X ± S)

| Groups | | Number of animals after termination of treatment | Hemolysin (OD value) |
|---|---|---|---|
| Ginsenoside rg3 derivatives | Low-dosage group | 6 | 0.17 ± 0.08 |
| | Medium-dosage group | 7 | 0.18 ± 0.07 |
| | High-dosage group | 9 | 0.19 ± 0.11 |

The experiment proves that all the ginseng alcohol extracts, the ginseng water extracts, the ginseng total ginsenoside, the panaxdiol type ginsenoside, the ginsenoside rg3 and the ginsenoside rg3 derivatives have the effect of improving serum hemolysin antibodies of the HCMV infected mice, compared with the model group, there are significant differences. Particularly, the level of the serum hemolysin antibodies of the ginseng water extract, ginseng total ginsenoside, panaxdiol type ginsenoside, ginsenoside rg3 and ginsenoside rg3 derivative groups is superior to that of the positive drug control group, which states that the ginseng water extract, total ginsenoside, panaxdiol type ginsenoside, ginsenoside rg3 and ginsenoside rg3 derivative groups have a stronger therapeutic effect on HCMV-infected mice than the positive drug.

The invention claimed is:

1. A method for treating human cytomegalovirus (HCMV) infection in a patient, comprising administering a therapeutically effective amount of isolated ginsenoside rg3 or isolated 20(R)-ginsenoside Rg3 8-N-butyrate absent other active ingredients having anti-HCMV activity the patient, wherein HCMV infection is treated in the patient.

2. The method of claim 1, characterized in that the isolated ginsenoside rg3 or the isolated 20(R)-ginsenoside Rg3 8-N-butyrate is administered in a pharmaceutically acceptable carrier.

3. The method of claim 1, characterized in that the isolated ginsenoside rg3 or the isolated 20(R)-ginsenoside Rg3 8-N-butyrate is in the form of tablets, capsules, pills, powder, granules, syrups, solutions, emulsions, injections, sprays, aerosols, gels, creams, tinctures, cataplasm, rubber emplastrum or emplastrum.

4. The method of claim 1, characterized in that the isolated ginsenoside rg3 is 20(R)-ginsenoside rg3.

* * * * *